United States Patent [19]

Foncerrada et al.

[11] Patent Number: 5,366,892

[45] Date of Patent: Nov. 22, 1994

[54] GENE ENCODING A COLEOPTERAN-ACTIVE TOXIN

[75] Inventors: Luis Foncerrada, Vista; August J. Sick, Oceanside; Jewel M. Payne, Davis, all of Calif.

[73] Assignee: Mycogen Corporation, San Diego, Calif.

[21] Appl. No.: 812,180

[22] Filed: Jan. 2, 1992

Related U.S. Application Data

[63] Continuation-in-part of Ser. No. 642,112, Jan. 16, 1991, Pat. No. 5,277,905.

[51] Int. Cl.$^5$ .................... A01N 63/00; C12N 1/21; C12N 15/70; C12N 15/32
[52] U.S. Cl. .................... 435/252.33; 424/93.2; 435/172.3; 435/252.34; 435/252.3; 435/320.1; 536/23.71
[58] Field of Search ............... 435/240.2, 240.4, 252.3, 435/252.31, 252.33, 252.34, 254, 255, 320.1, 172.3; 424/93 A, 93 B, 93 D, 93 K, 93 L, 93 M, 93 N, 93 P, 93 Q, 93 S, 93 U; 536/23.71

[56] References Cited

U.S. PATENT DOCUMENTS

| | | | |
|---|---|---|---|
| 4,910,016 | 3/1990 | Gaertner et al. | 424/93 L |
| 4,966,765 | 10/1990 | Payne et al. | 924/93 L |

FOREIGN PATENT DOCUMENTS

| | | | |
|---|---|---|---|
| 0202739 | 11/1986 | European Pat. Off. | A01N 63/00 |
| 0324254 | 7/1989 | European Pat. Off. | A01N 63/00 |
| 0328383 | 8/1989 | European Pat. Off. | A01N 63/00 |
| 0330342 | 8/1989 | European Pat. Off. | A01N 63/00 |
| 0337604 | 10/1989 | European Pat. Off. | C12N 15/00 |
| 0382990 | 8/1990 | European Pat. Off. | C12N 15/32 |

OTHER PUBLICATIONS

Lereclus et al., FEMS Micro. Lett. 60: 211–218 (1989).
Couch, T. L. (1980) "Mosquito Pathogenicity of *Bacillus thuringiensis* var. *israelensis*," *Eveloments in Industrial Microbiolog* 22:61–76.
Beegle, C. C., (1978) "Use of Entomogenous Bacteria in Agroecosystems," *Developments in Industrial Microbiology* 20:97–104.
Krieg, Von A., (1983) "*Bacillus thuringiensis* var. *tenebrionis*: ein neuer, gegenuber Larven von Coleopteran wirksamer Pathotype" *Journal of Applied Entomology*, 96:500–508.

*Primary Examiner*—Richard A. Schwartz
*Assistant Examiner*—Nancy T. Vogel
*Attorney, Agent, or Firm*—Saliwanchik & Saliwanchik

[57] ABSTRACT

The subject invention concerns a novel microbe and gene encoding a novel toxin protein with activity against insect pests of the order Coleoptera. Pests in the order Coleoptera do heavy damage to crops, e.g., corn. The novel *Bacillus thuringiensis* microbe of the invention is referred to as *B.t.* PS50C. The spores or crystals of this microbe, or mutants thereof, are useful to control coleopteran pests in various environments. The novel gene of the invention can be used to transform various hosts wherein the novel toxic protein can be expressed.

11 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3471 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Bacillus thuringiensis
        ( B ) STRAIN: kumamotoensis
        ( C ) INDIVIDUAL ISOLATE: PS50C     ( v i i ) IMMEDIATE SOURCE:
        ( A ) LIBRARY: LAMBDAGEM (TM) - 11 LIBRARY OF LUIS FONCERRADA
        ( B ) CLONE: 50C     ( x i ) SEQUENCE DESCRIPTION: SEQ ID NO:1:

```
ATGAGTCCAA  ATAATCAAAA  TGAATATGAA  ATTATAGATG  CGACACCTTC  TACATCTGTA      60
TCCAGTGATT  CTAACAGATA  CCCTTTTGCG  AATGAGCCAA  CAGATGCGTT  ACAAAATATG     120
AATTATAAAG  ATTATCTGAA  AATGTCTGGG  GGAGAGAATC  CTGAATTATT  TGGAAATCCG     180
GAGACGTTTA  TTAGTTCATC  CACGATTCAA  ACTGGAATTG  GCATTGTTGG  TCGAATACTA     240
GGAGCTTTAG  GGGTTCCATT  TGCTAGTCAG  ATAGCTAGTT  TCTATAGTTT  CATTGTTGGT     300
CAATTATGGC  CGTCAAAGAG  CGTAGATATA  TGGGGAGAAA  TTATGGAACG  AGTGGAAGAA     360
CTCGTTGATC  AAAAAATAGA  AAAATATGTA  AAAGATAAGG  CTCTTGCTGA  ATTAAAGGG     420
CTAGGAAATG  CTTTGGATGT  ATATCAGCAG  TCACTTGAAG  ATTGGCTGGA  AAATCGCAAT     480
GATGCAAGAA  CTAGAAGTGT  TGTTTCTAAT  CAATTTATAG  CTTTAGATCT  TAACTTTGTT     540
AGTTCAATTC  CATCTTTTGC  AGTATCCGGA  CACGAAGTAC  TATTATTAGC  AGTATATGCA     600
```

| | | | | | |
|---|---|---|---|---|---|
| CAGGCTGTGA | ACCTACATTT | ATTGTTATTA | AGAGATGCTT | CTATTTTTGG | AGAAGAGTGG | 660 |
| GGATTTACAC | CAGGTGAAAT | TTCTAGATTT | TATAATCGTC | AAGTGCAACT | TACCGCTGAA | 720 |
| TATTCAGACT | ATTGTGTAAA | GTGGTATAAA | ATCGGCTTAG | ATAAATTGAA | AGGTACCACT | 780 |
| TCTAAAAGTT | GGCTGAATTA | TCATCAGTTC | CGTAGAGAGA | TGACATTACT | GGTATTAGAT | 840 |
| TTGGTGGCGT | TATTTCCAAA | CTATGACACA | CATATGTATC | CAATCGAAAC | AACAGCTCAA | 900 |
| CTTACACGGG | ATGTGTATAC | AGATCCGATA | GCATTAACA | TAGTGACAAG | TACTGGATTC | 960 |
| TGCAACCCTT | GGTCAACCCA | CAGTGGTATT | CTTTTTATG | AAGTTGAAAA | CAACGTAATT | 1020 |
| CGTCCGCCAC | ACTTGTTTGA | TATACTCAGC | TCAGTAGAAA | TTAATACAAG | TAGAGGGGGT | 1080 |
| ATTACGTTAA | ATAATGATGC | ATATATAAAC | TACTGGTCAG | GACATACCCT | AAAATATCGT | 1140 |
| AGAACAGCTG | ATTCGACCGT | AACATACACA | GCTAATTACG | GTCGAATCAC | TTCAGAAAAG | 1200 |
| AATTCATTTG | CACTTGAGGA | TAGGGATATT | TTTGAATTA | ATTCAACTGT | GGCAAACCTA | 1260 |
| GCTAATTACT | ACCAAAGGC | ATATGGTGTG | CCGGGATCTT | GGTTCCATAT | GGTAAAAGG | 1320 |
| GGAACCTCAT | CAACAACAGC | GTATTTATAT | TCAAAACAC | ATACAGCTCT | CCAAGGGTGT | 1380 |
| ACACAGGTTT | ATGAATCAAG | TGATGAAATA | CCTCTAGATA | GAACTGTACC | GGTAGCTGAA | 1440 |
| AGCTATAGTC | ATAGATTATC | TCATATTACC | TCCCATTCTT | TCTCTAAAAA | TGGGAGTGCA | 1500 |
| TACTATGGGA | GTTTCCCTGT | ATTTGTTGG | ACACATACTA | GTGCGGATTT | AAATAATACA | 1560 |
| ATATATTCAG | ATAAAATCAC | TCAAATTCCA | GCGGTAAAGG | GAGACATGTT | ATATCTAGGG | 1620 |
| GGTTCCGTAG | TACAGGGTCC | TGGATTTACA | GGAGGAGATA | TATTAAAAAG | AACCAATCCT | 1680 |
| AGCATATTAG | GGACCTTTGC | GGTTACAGTA | AATGGGTCGT | TATCACAAAG | ATATCGTGTA | 1740 |
| AGAATTCGCT | ATGCCTCTAC | AACAGATTTT | GAATTACTC | TATACCTTGG | CGACACAATA | 1800 |
| GAAAAAAATA | GATTTAACAA | AACTATGGAT | AATGGGGCAT | CTTTAACGTA | TGAAACATTT | 1860 |
| AAATTCGCAA | GTTTCATTAC | TGATTTCCAA | TTCAGAGAAA | CACAAGATAA | AATACTCCTA | 1920 |
| TCCATGGGTG | ATTTTAGCTC | CGGTCAAGAA | GTTTATATAG | ACCGAATCGA | ATTCATCCCA | 1980 |
| GTAGATGAGA | CATATGAGGC | GGAACAAGAT | TTAGAAGCGG | CGAAGAAAGC | AGTGAATGCC | 2040 |
| TTGTTTACGA | ATACAAAAGA | TGGCTTACGA | CCAGGTGTAA | CGGATTATGA | AGTAAATCAA | 2100 |
| GCGGCAAACT | TAGTGGAATG | CCTATCGGAT | GATTTATATC | CAAATGAAAA | ACGATTGTTA | 2160 |
| TTTGATGCGG | TGAGAGAGGC | AAAACGCCTC | AGTGGGGCAC | GTAACTTACT | ACAAGATCCA | 2220 |
| GATTTCCAAG | AGATAAACGG | AGAAAATGGA | TGGGCGGCAA | GTACGGGAAT | TGAGATTGTA | 2280 |
| GAAGGGGATG | CTGTATTTAA | AGGACGTTAT | CTACGCCTAC | CAGGTGCACG | AGAAATTGAT | 2340 |
| ACGGAAACGT | ATCCAACGTA | TCTGTATCAA | AAAGTAGAGG | AAGGTGTATT | AAAACCATAC | 2400 |
| ACAAGATATA | GACTGAGAGG | GTTTGTGGGA | AGTAGTCAAG | GATTAGAAAT | TTATACGATA | 2460 |
| CGTCACCAAA | CGAATCGAAT | TGTAAAGAAT | GTACCAGATG | ATTTATTGCC | AGATGTATCT | 2520 |
| CCTGTAAACT | CTGATGGCAG | TATCAATCGA | TGCAGCGAAC | AAAAGTATGT | GAATAGCCGT | 2580 |
| TTAGAAGGAG | AAAACCGTTC | TGGTGATGCA | CATGAGTTCT | CGCTCCCTAT | CGATATAGGA | 2640 |
| GAGCTGGATT | ACAATGAAAA | TGCAGGAATA | TGGGTTGGAT | TAAGATTAC | GGACCCAGAG | 2700 |
| GGATACGCAA | CACTTGGAAA | TCTTGAATTA | GTCGAAGAGG | GACCTTTGTC | AGGAGACGCA | 2760 |
| TTAGAGCGCT | TGCAAAGAGA | AGAACAACAG | TGGAAGATTC | AAATGACAAG | AAGACGTGAA | 2820 |
| GAGACAGATA | GAAGATACAT | GGCATCGAAA | CAAGCGGTAG | ATCGTTTATA | TGCCGATTAT | 2880 |
| CAGGATCAAC | AACTGAATCC | TGATGTAGAG | ATTACAGATC | TTACTGCGGC | TCAAGATCTG | 2940 |
| ATACAGTCCA | TTCCTTACGT | ATATAACGAA | ATGTTCCCAG | AAATACCAGG | GATGAACTAT | 3000 |
| ACGAAGTTTA | CAGAATTAAC | AGATCGACTC | CAACAAGCGT | GGAATTTGTA | TGATCAGCGA | 3060 |

-continued

```
AATGCCATAC CAAATGGTGA TTTTCGAAAT GGGTTAAGTA ATTGGAATGC AACGCCTGGC   3120
GTAGAAGTAC AACAAATCAA TCATACATCT GTCCTTGTGA TTCCAAACTG GGATGAACAA   3180
GTTTCACAAC AGTTTACAGT TCAACCGAAT CAAAGATATG TATTACGAGT TACTGCAAGA   3240
AAAGAAGGGG TAGGAAATGG ATATGTAAGT ATTCGTGATG GTGGAAATCA ATCAGAAACG   3300
CTTACTTTTA GTGCAAGCGA TTATGATACA AATGGTGTGT ATAATGACCA AACCGGCTAT   3360
ATCACAAAAA CAGTGACATT CATCCCGTAT ACAGATCAAA TGTGGATTGA AATAAGTGAA   3420
ACAGAAGGTA CGTTCTATAT AGAAAGTGTA GAATTGATTG TAGACGTAGA G            3471
```

( 2 ) INFORMATION FOR SEQ ID NO:2:

( i ) SEQUENCE CHARACTERISTICS:
( A ) LENGTH: 1157 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: PS50C ( v i i ) IMMEDIATE SOURCE:
( A ) LIBRARY: Lambdagem (TM) - 11 LIBRARY OF LUIS FONCERRADA
( B ) CLONE: 50C ( x i ) SEQUENCE DESCRIPTION: SEQ ID NO:2:

```
Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
            20                  25                  30

Pro Thr Asp Ala Leu Gln Asn Met Asn Tyr Lys Asp Tyr Leu Lys Met
        35                  40                  45

Ser Gly Gly Glu Asn Pro Glu Leu Phe Gly Asn Pro Glu Thr Phe Ile
    50                  55                  60

Ser Ser Ser Thr Ile Gln Thr Gly Ile Gly Ile Val Gly Arg Ile Leu
65                  70                  75                  80

Gly Ala Leu Gly Val Pro Phe Ala Ser Gln Ile Ala Ser Phe Tyr Ser
                85                  90                  95

Phe Ile Val Gly Gln Leu Trp Pro Ser Lys Ser Val Asp Ile Trp Gly
            100                 105                 110

Glu Ile Met Glu Arg Val Glu Glu Leu Val Asp Gln Lys Ile Glu Lys
        115                 120                 125

Tyr Val Lys Asp Lys Ala Leu Ala Glu Leu Lys Gly Leu Gly Asn Ala
    130                 135                 140

Leu Asp Val Tyr Gln Gln Ser Leu Glu Asp Trp Leu Glu Asn Arg Asn
145                 150                 155                 160

Asp Ala Arg Thr Arg Ser Val Val Ser Asn Gln Phe Ile Ala Leu Asp
                165                 170                 175

Leu Asn Phe Val Ser Ser Ile Pro Ser Phe Ala Val Ser Gly His Glu
            180                 185                 190

Val Leu Leu Leu Ala Val Tyr Ala Gln Ala Val Asn Leu His Leu Leu
        195                 200                 205

Leu Leu Arg Asp Ala Ser Ile Phe Gly Glu Glu Trp Gly Phe Thr Pro
```

-continued

```
              210                          215                          220
Gly  Glu  Ile  Ser  Arg  Phe  Tyr  Asn  Arg  Gln  Val  Gln  Leu  Thr  Ala  Glu
225                      230                      235                      240

Tyr  Ser  Asp  Tyr  Cys  Val  Lys  Trp  Tyr  Lys  Ile  Gly  Leu  Asp  Lys  Leu
                    245                      250                      255

Lys  Gly  Thr  Thr  Ser  Lys  Ser  Trp  Leu  Asn  Tyr  His  Gln  Phe  Arg  Arg
               260                      265                      270

Glu  Met  Thr  Leu  Leu  Val  Leu  Asp  Leu  Val  Ala  Leu  Phe  Pro  Asn  Tyr
              275                      280                      285

Asp  Thr  His  Met  Tyr  Pro  Ile  Glu  Thr  Thr  Ala  Gln  Leu  Thr  Arg  Asp
     290                      295                      300

Val  Tyr  Thr  Asp  Pro  Ile  Ala  Phe  Asn  Ile  Val  Thr  Ser  Thr  Gly  Phe
305                      310                      315                      320

Cys  Asn  Pro  Trp  Ser  Thr  His  Ser  Gly  Ile  Leu  Phe  Tyr  Glu  Val  Glu
                    325                      330                      335

Asn  Asn  Val  Ile  Arg  Pro  Pro  His  Leu  Phe  Asp  Ile  Leu  Ser  Ser  Val
               340                      345                      350

Glu  Ile  Asn  Thr  Ser  Arg  Gly  Gly  Ile  Thr  Leu  Asn  Asn  Asp  Ala  Tyr
              355                      360                      365

Ile  Asn  Tyr  Trp  Ser  Gly  His  Thr  Leu  Lys  Tyr  Arg  Arg  Thr  Ala  Asp
     370                      375                      380

Ser  Thr  Val  Thr  Tyr  Thr  Ala  Asn  Tyr  Gly  Arg  Ile  Thr  Ser  Glu  Lys
385                      390                      395                      400

Asn  Ser  Phe  Ala  Leu  Glu  Asp  Arg  Asp  Ile  Phe  Glu  Ile  Asn  Ser  Thr
                    405                      410                      415

Val  Ala  Asn  Leu  Ala  Asn  Tyr  Tyr  Gln  Lys  Ala  Tyr  Gly  Val  Pro  Gly
               420                      425                      430

Ser  Trp  Phe  His  Met  Val  Lys  Arg  Gly  Thr  Ser  Ser  Thr  Thr  Ala  Tyr
              435                      440                      445

Leu  Tyr  Ser  Lys  Thr  His  Thr  Ala  Leu  Gln  Gly  Cys  Thr  Gln  Val  Tyr
     450                      455                      460

Glu  Ser  Ser  Asp  Glu  Ile  Pro  Leu  Asp  Arg  Thr  Val  Pro  Val  Ala  Glu
465                      470                      475                      480

Ser  Tyr  Ser  His  Arg  Leu  Ser  His  Ile  Thr  Ser  His  Ser  Phe  Ser  Lys
                    485                      490                      495

Asn  Gly  Ser  Ala  Tyr  Tyr  Gly  Ser  Phe  Pro  Val  Phe  Val  Trp  Thr  His
               500                      505                      510

Thr  Ser  Ala  Asp  Leu  Asn  Asn  Thr  Ile  Tyr  Ser  Asp  Lys  Ile  Thr  Gln
              515                      520                      525

Ile  Pro  Ala  Val  Lys  Gly  Asp  Met  Leu  Tyr  Leu  Gly  Gly  Ser  Val  Val
     530                      535                      540

Gln  Gly  Pro  Gly  Phe  Thr  Gly  Gly  Asp  Ile  Leu  Lys  Arg  Thr  Asn  Pro
545                      550                      555                      560

Ser  Ile  Leu  Gly  Thr  Phe  Ala  Val  Thr  Val  Asn  Gly  Ser  Leu  Ser  Gln
                    565                      570                      575

Arg  Tyr  Arg  Val  Arg  Ile  Arg  Tyr  Ala  Ser  Thr  Thr  Asp  Phe  Glu  Phe
               580                      585                      590

Thr  Leu  Tyr  Leu  Gly  Asp  Thr  Ile  Glu  Lys  Asn  Arg  Phe  Asn  Lys  Thr
              595                      600                      605

Met  Asp  Asn  Gly  Ala  Ser  Leu  Thr  Tyr  Glu  Thr  Phe  Lys  Phe  Ala  Ser
     610                      615                      620

Phe  Ile  Thr  Asp  Phe  Gln  Phe  Arg  Glu  Thr  Gln  Asp  Lys  Ile  Leu  Leu
625                      630                      635                      640

Ser  Met  Gly  Asp  Phe  Ser  Ser  Gly  Gln  Glu  Val  Tyr  Ile  Asp  Arg  Ile
                    645                      650                      655
```

```
Glu Phe Ile Pro Val Asp Glu Thr Tyr Glu Ala Glu Gln Asp Leu Glu
            660             665             670

Ala Ala Lys Lys Ala Val Asn Ala Leu Phe Thr Asn Thr Lys Asp Gly
        675             680             685

Leu Arg Pro Gly Val Thr Asp Tyr Glu Val Asn Gln Ala Ala Asn Leu
        690             695             700

Val Glu Cys Leu Ser Asp Asp Leu Tyr Pro Asn Glu Lys Arg Leu Leu
705             710             715                         720

Phe Asp Ala Val Arg Glu Ala Lys Arg Leu Ser Gly Ala Arg Asn Leu
                725             730                 735

Leu Gln Asp Pro Asp Phe Gln Glu Ile Asn Gly Glu Asn Gly Trp Ala
            740             745             750

Ala Ser Thr Gly Ile Glu Ile Val Glu Gly Asp Ala Val Phe Lys Gly
        755             760             765

Arg Tyr Leu Arg Leu Pro Gly Ala Arg Glu Ile Asp Thr Glu Thr Tyr
    770             775             780

Pro Thr Tyr Leu Tyr Gln Lys Val Glu Glu Gly Val Leu Lys Pro Tyr
785             790             795                         800

Thr Arg Tyr Arg Leu Arg Gly Phe Val Gly Ser Ser Gln Gly Leu Glu
            805             810                 815

Ile Tyr Thr Ile Arg His Gln Thr Asn Arg Ile Val Lys Asn Val Pro
            820             825             830

Asp Asp Leu Leu Pro Asp Val Ser Pro Val Asn Ser Asp Gly Ser Ile
        835             840             845

Asn Arg Cys Ser Glu Gln Lys Tyr Val Asn Ser Arg Leu Glu Gly Glu
    850             855             860

Asn Arg Ser Gly Asp Ala His Glu Phe Ser Leu Pro Ile Asp Ile Gly
865             870             875                         880

Glu Leu Asp Tyr Asn Glu Asn Ala Gly Ile Trp Val Gly Phe Lys Ile
            885             890             895

Thr Asp Pro Glu Gly Tyr Ala Thr Leu Gly Asn Leu Glu Leu Val Glu
            900             905             910

Glu Gly Pro Leu Ser Gly Asp Ala Leu Glu Arg Leu Gln Arg Glu Glu
        915             920             925

Gln Gln Trp Lys Ile Gln Met Thr Arg Arg Arg Glu Glu Thr Asp Arg
        930             935             940

Arg Tyr Met Ala Ser Lys Gln Ala Val Asp Arg Leu Tyr Ala Asp Tyr
945             950             955                         960

Gln Asp Gln Gln Leu Asn Pro Asp Val Glu Ile Thr Asp Leu Thr Ala
            965             970             975

Ala Gln Asp Leu Ile Gln Ser Ile Pro Tyr Val Tyr Asn Glu Met Phe
        980             985             990

Pro Glu Ile Pro Gly Met Asn Tyr Thr Lys Phe Thr Glu Leu Thr Asp
        995             1000            1005

Arg Leu Gln Gln Ala Trp Asn Leu Tyr Asp Gln Arg Asn Ala Ile Pro
    1010            1015            1020

Asn Gly Asp Phe Arg Asn Gly Leu Ser Asn Trp Asn Ala Thr Pro Gly
1025            1030            1035                        1040

Val Glu Val Gln Gln Ile Asn His Thr Ser Val Leu Val Ile Pro Asn
            1045            1050            1055

Trp Asp Glu Gln Val Ser Gln Gln Phe Thr Val Gln Pro Asn Gln Arg
            1060            1065            1070

Tyr Val Leu Arg Val Thr Ala Arg Lys Glu Gly Val Gly Asn Gly Tyr
        1075            1080            1085
```

```
Val Ser Ile Arg Asp Gly Gly Asn Gln Ser Glu Thr Leu Thr Phe Ser
    1090                1095            1100

Ala Ser Asp Tyr Asp Thr Asn Gly Val Tyr Asn Asp Gln Thr Gly Tyr
1105                1110              1115                1120

Ile Thr Lys Thr Val Thr Phe Ile Pro Tyr Thr Asp Gln Met Trp Ile
                1125            1130                1135

Glu Ile Ser Glu Thr Glu Gly Thr Phe Tyr Ile Glu Ser Val Glu Leu
            1140                1145            1150

Ile Val Asp Val Glu
        1155
```

GENE ENCODING A COLEOPTERAN-ACTIVE TOXIN

CROSS-REFERENCE TO RELATED APPLICATION

This is a continuation in part of co-pending application Ser. No. 07/642,112, filed Jan. 16, 1991, U.S. Pat. No. 5,277,905.

BACKGROUND OF THE INVENTION

*Bacillus thuringiensis* (*B.t.*) produces an insect toxin designated as δ-endotoxin. It is synthesized by the *B.t.* sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," Developments in Industrial Microbiology 20:97–104. Krieg, et al., Z. ang. Ent. (1983) 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata* and *Agelastica alni*.

In European Patent Application 0 202 739 there is disclosed a novel *B.t.* isolate active against Coleoptera. It is known as *B. thuringiensis* var. *san diego* (*B.t.sd.*). U.S. Pat. No. 4,966,765 discloses the coleopteran-active *Bacillus thuringiensis* isolate *B.t.* PS86B1. European Patent Application 0 337 604 also discloses a novel *B.t.* isolate active against Coleoptera. This isolate is *B.t.* PS43F.

Coleopteran-active strains, such as *B.t.sd.*, *B.t.* PS86B1, and *B.t.* PS43F, can be used to control foliar-feeding beetles. The Colorado potato beetle (*Leptinotarsa decemlineata*), for example, is susceptible to the delta-endotoxin of *B.t.sd.* and larvae are killed upon ingesting a sufficient dose of spore/crystal preparation on treated foliage.

A number of crops are attacked by flea beetles. These beetles belong to the family Chrysomelidae, the decemlineata. The adults can cause extensive damage by feeding on the foliage.

BRIEF SUMMARY OF THE INVENTION

The subject invention concerns a novel *Bacillus thuringiensis* (*B.t.*) isolate and a cloned gene therefrom which encodes a novel coleopteran-active protein. The novel *B.t.* isolate, known herein as *Bacillus thuringiensis* PS50C (*B.t.* PS50C), has thus far been shown to be active against the Colorado potato beetle (*Leptinotarsa decemlineata*). The novel δ-endotoxin gene of the invention encodes an ≈130 kDa protein. The nucleotide sequence of the gene (open reading frame only) is shown in Sequence ID No. 1. The predicted peptide sequence of the toxin is shown in Sequence ID No. 2.

The subject invention also includes mutants of *B.t.* PS50C which have substantially the same pesticidal properties as *B.t.* PS50C. Procedures for making mutants are well known in the microbiological art. Ultraviolet light and nitrosoguanidine are used extensively toward this end.

Further, the invention also includes the treatment of substantially intact *B.t.* PS50C cells, and recombinant cells containing the gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

BRIEF DESCRIPTION OF THE SEQUENCES

Sequence ID No. 1 is the nucleotide sequence (open reading frame only) of the novel gene of the invention.

Sequence ID No. 2 is the predicted peptide sequence of the toxin.

DETAILED DISCLOSURE OF THE INVENTION

The novel *Bacillus thuringiensis* isolate of the subject invention has the following characteristics in its biologically pure form:

Characteristics of *B.t.* PS50C

Colony morphology—Large colony, dull surface, typical *B.t.*

Vegetative cell morphology—typical *B.t.*

Culture methods—typical for *B.t.*

Flagellar serotyping—PS50C belongs to serotype 18, kumamotoensis.

Crystal morphology—a sphere.

RFLP analysis—Southern hybridization of total DNA distinguishes *B.t.* PS50C from *B.t.sd.* and other *B.t.* isolates.

Alkali-soluble proteins-SDS polyacrylamide gel electrophoresis (SDS-PAGE) shows a 130 kDa doublet protein.

A comparison of the characteristics of *B. thuringiensis* PS50C (*B.t.* PS50C) to the characteristics of the known *B.t.* strains *B. thuringiensis* var. *san diego* (*B.t.sd.*), *B. thuringiensis* PS86B1 (NRRL B-18299), and *B. thuringiensis* var. *kurstaki* (HD-1) is shown in Table 1.

TABLE 1

| Comparison of B.t. PS50C, B.t. PS86B1, B.t.sd., and B.t. HD-1 | | | | |
|---|---|---|---|---|
| | B.t. PS50C | B.t.sd. | B.t. PS86B1 | B.t. HD-1 |
| Serovar | kumamotoensis | morrisoni | tolworthi | kurstaki |
| Type of inclusion | sphere | square wafer | flat, pointed ellipse, plus sm. inclusions | Bipyramid |

TABLE 1-continued

Comparison of B.t. PS50C, B.t. PS86B1, B.t.sd., and B.t. HD-1

|  | B.t. PS50C | B.t.sd. | B.t. PS86B1 | B.t. HD-1 |
|---|---|---|---|---|
| Size of alkali-soluble proteins by SDS-PAGE | 130 kDa doublet | 72,000<br>64,000 | 75,000<br>68,000<br>61,000 | 130,000<br>68,000 |
| Host range | Coleoptera | Coleoptera | Coleoptera | Lepidoptera |

The cultures disclosed in this application have been deposited in the Agricultural Research Service Patent Culture Collection (NRRL), Northern Regional Research Center, 1815 North University Street, Peoria, Ill. 61604, USA.

| Culture | Repository No. | Deposit date |
|---|---|---|
| *Bacillus thuringiensis* PS50C | NRRL B-18746 | January 9, 1991 |
| *Escherichia coil* NM522 [pMYC1638] | NRRL B-18751 | January 11, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

*B.t.* PS50C, NRRL B-18746, can be cultured using standard art media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

Figure 1:
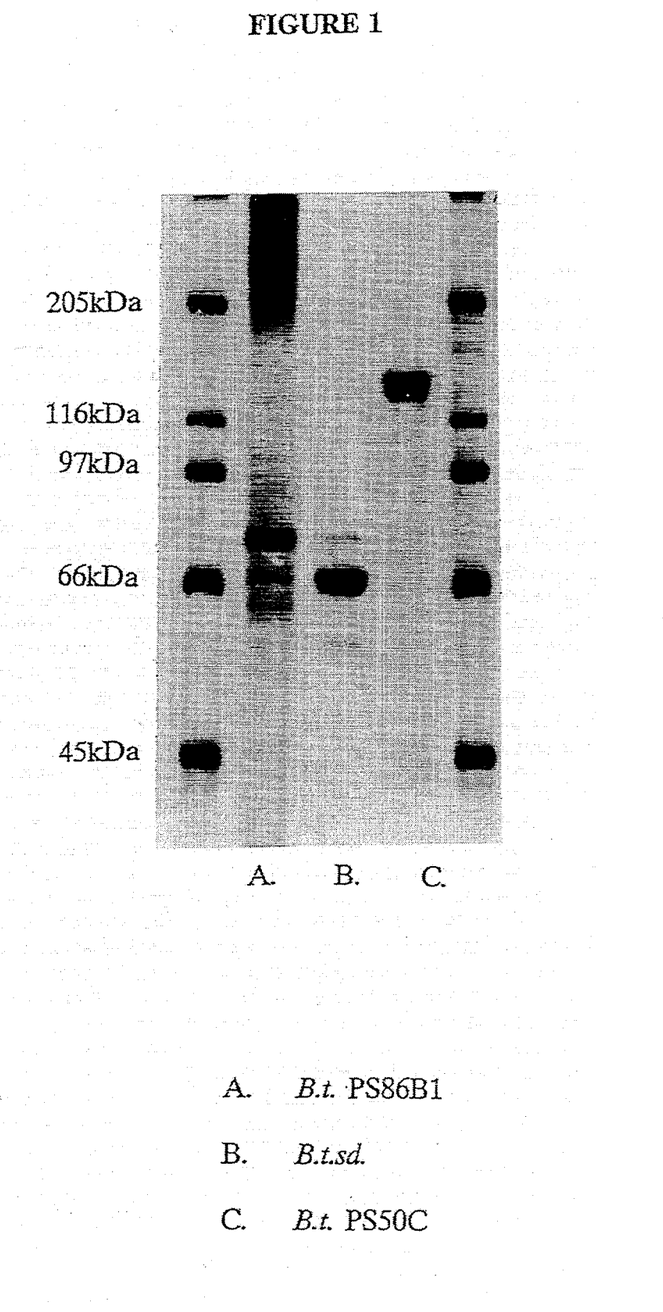
FIG. 1—Photograph of a Standard SDS Polyacrylamide Gel of *B.t.* PS50C, *B.t.sd.*, and *B.t.* PS86B1.
Figure 2:
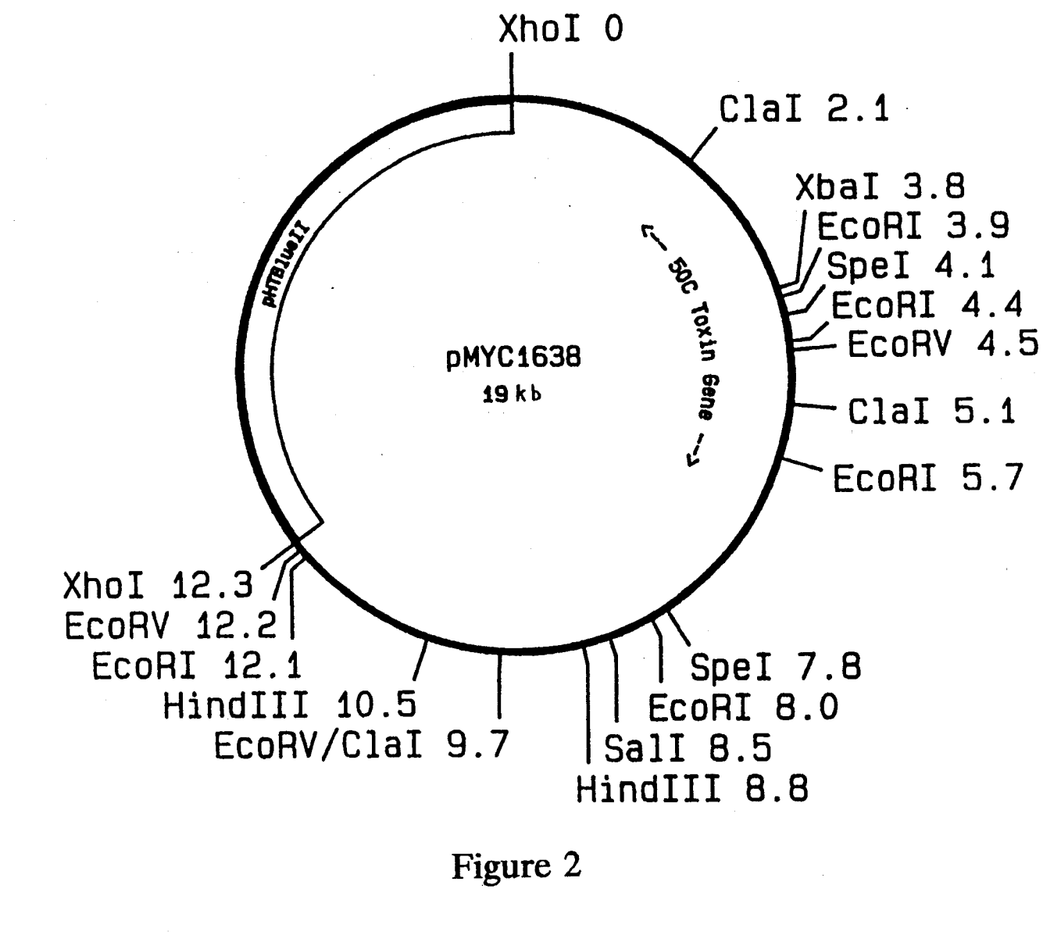
FIG. 2—Restriction map of pMYC1638.

Plasmid DNA (pMYC1638) containing the toxin gene from *B.t.* PS50C can be purified from *E. coli* NM522[pMYC1638] by standard procedures well known in the art. The toxin gene can be excised from the plasmid DNA by restriction enzyme digestion, as indicated in FIG. 2.

Formulated products can be sprayed or applied onto foliage to control phytophagous beetles or caterpillars.

Another approach that can be taken is to incorporate the spores and crystals of *B.t.* PS50C into bait granules containing an attractant and applying these granules to the soil for control of soil-inhabiting Coleoptera. Formulated *B.t.* PS50C can also be applied as a seed-coating or root treatment or total plant treatment.

The *B.t.* PS50C cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humanson, Gretchen. L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

The novel toxin gene of the subject invention was obtained from a novel coleopteran-active *B. thuringiensis* (*B.t.*) isolate designated *B.t.* PS50C. The gene was isolated as disclosed in the Examples.

The toxin gene of the subject invention can be introduced into a wide variety of microbial hosts. Expression of the toxin gene results, directly or indirectly, in the intracellular production and maintenance of the pesticide. With suitable hosts, e.g., Psuedomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulator region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no function replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Exchericha coli, Bacillus subtilis, Streptomyces lividans*, and the like.

The cell will usually be intact and be substantially in the proliferative form when treated, rather than in a spore form, although in some instances spores may be employed.

Treatment of the recombinant microbial cell can be done as disclosed infra. The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention.

These examples should not be construed as limiting. All percentages are by weight and all solvent mixture proportions are by volume unless otherwise noted.

EXAMPLE 1

Culturing B.t. PS50C, NRRL B-18746

A subculture of B.t. PS50C, NRRL B-18746 can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Testing of B.t. PS50C, NRRL B-18746 Spores and Crystals

B.t. PS50C, NRRL B-18746 spores and crystals are toxic to the Colorado potato beetle (CPB). The assay for the Colorado potato beetle was conducted as follows:

CPB Bioassay—Early second instar larvae of *Leptinotarsa decemlineata* are placed on potato leaves which have been dipped in suspension containing *Bacillus thuringiensis* preparations. The larvae are incubated at 25° C. for 4 days, and larval mortality is recorded and analyzed using probit analysis.

EXAMPLE 3

Cloning of a Novel Toxin Gene from B.t. Isolate PS50C

Total cellular DNA was prepared from *Bacillus thuringiensis* (B.t.) cells grown to an optical density, at 600 nm, of 1.0. The cells were recovered by centrifugation and protoplasts were prepared in TES buffer (30 mM Tris-HCl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). Nucleic acids were precipitated with ethanol and DNA was purified by isopycnic banding on cesium chloride-ethidium bromide gradients.

Total cellular DNA from B.t. subsp. kumamotoensis (B.t.kum.), isolate PS50C, was digested with HindIII and fractionated by electrophoresis on a 0.8% (w/v) agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe. Results showed that the hybridizing fragments of PS50C are approximately 12 Kb and 1.7 Kb in size.

A library was constructed from PS50C total cellular DNA partially digested with Sau3A and size fractionated by gel electrophoresis. The 9-23 Kb region of the gel was excised and the DNA was electroeluted and then concentrated using an Elutip-d ™ ion exchange column (Schleicher and Schuel, Keene, N.H.). The isolated Sau3A fragments were ligated into BamHI-digested LambdaGEM-11 ™ (PROMEGA). The packaged phage was plated on *E. coli* KW251 cells (PROMEGA) at a high titer and screened using the radiolabled oligonucleotide probe. Hybridizing plaques were purified and rescreened at a lower plaque density. Single isolated, purified plaques that hybridized with the probe were used to infect *E. coli* KW251 cells in liquid culture for preparation of phage for DNA isolation. DNA was isolated by standard procedures. Preparative amounts of DNA were digested with XhoI (to release the inserted DNA from lambda sequences) and separated by electrophoresis on a 0.6% agarose-TAE gel. The large fragments were purified by ion exchange chromatography as above and ligated to XhoI-digested, dephosphorylated pHTBlueII (an *E.coli/B. thuringiensis* shuttle vector comprised of pBluescript s/k [Stratagene] and the replication origin from a resident B.t. plasmid [D. Lereclus et al. 1989. FEMS Microbiology Letters 60:211-218]). The ligation mix was introduced by transformation into competent *E.* coli NM522 cells (ATCC 47000) and plated on LB agar containing ampicillin, isopropyl-(β)-D-thiogalactoside (IPTG) and 5-bromo-4-chloro-4-indolyl-(β)-D-galactoside (XGAL). White colonies, with putative restriction fragment insertions in the (β)-galactosidase gene of pHTBlueII, were subjected to standard rapid plasmid purification procedures. Plasmids were analyzed by XhoI digestion and agarose gel electrophoresis. The desired plasmid construct, pMYC1638, contains an approximately 12 Kb XhoI insert. A partial restriction map (FIG. 2) of the cloned insert indicates that the toxin gene is novel compared to the maps of other toxin genes encoding insecticidal proteins. The nucleotide sequence (open reading frame only) is shown in Sequence ID No. 1. The predicted peptide sequence of the toxin is shown in Sequence ID No. 2.

Plasmid pMYC1638 was introduced into an acrystalliferous (Cry−) B.t. host (HD-1 cryB obtained from A. Aronson, Purdue University) by electroporation. Expression of an approximately 130 kDa protein was verified by SDS-PAGE. Broth containing spores and crystals was used for the determination of toxicity to *Keptinotarsa decemlineata*.

Plasmid pMYC1638 containing the B.t. gene, can be removed from the transformed host microbe by use of standard well-known procedures. For example, *E. coli* NM522[pMYC1638] NRRL B-18751 can be subjected to cleared lystae isopycnic density gradient procedures, and the like, to recover pMYC1638.

EXAMPLE 4

Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to generate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genest. The toxin gene, for example, can be inserted into the BamHI site of pEND4K, propagated in *E. coli*, and transformed into appropriate plant cells.

EXAMPLE 5

Cloning of Novel, *B. thuringiensis* Gene into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell Biol. 4:399–406), and pAC380, described by Smith et al. (Smith, G. E., Summers, M. D. and Fraser, M. J. [1983] Mol. Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

---

We claim:

1. An isolated polynucleotide encoding a *Bacillus thuringiensis* toxin active against coleopteran pests wherein said toxin has a molecular weight of ≈130 kDa and a predicted peptide sequence as shown in Sequence ID No. 2.

2. A recombinant DNA transfer vector comprising DNA which codes for a *Bacillus thuringiensis* toxin active against coleopteran pests wherein said toxin has a molecular weight of ≈130 kDa and a predicted peptide sequence as shown in Sequence ID No. 2.

3. An isolated polynucleotide DNA having the nucleotide sequence shown in Sequence ID No. 1.

4. *Escherichia coli* host transformed with a plasmid vector containing a *Bacillus thuringiensis* toxin gene encoding the *Bacillus thuringiensis* toxin active against coleopteran pests wherein said toxin has a molecular weight of ≈130 kDa and a predicted peptide sequence as shown in Sequence ID No. 2.

5. *Escherichia coli* NM522 (pMYC1638) a host according to claim 4.

6. A treated, substantially intact Pseudomonas cell containing an intracellular toxin, which toxin is a result of expression of a *Bacillus thuringiensis* toxin gene which codes for a polypeptide toxin active against coleopteran pests, wherein said toxin has a molecular weight of approximately 130 kDa and a predicted amino acid sequence as shown in SEQ ID No. 2, wherein said cell is treated under conditions which prolong the insecticidal activity when said cell is applied to the environment of a target insect.

7. A Pseudomonas cell according to claim 6, wherein said cell is treated with iodine.

8. The cell, according to claim 7, which is *Pseudomonas fluorescens*.

9. Plasmid denoted pMYC1638.

10. A root-colonizing bacterium transformed to express a *Bacillus thuringiensis* toxin active against coleopteran pests wherein said toxin has a molecular weight of approximately 130 kDa and a predicted amino acid sequence as shown in SEQ ID No. 2.

11. A method for controlling coleopteran insects which comprises administering to said insects or to the environment of said insects a root-colonizing bacterium transformed to express a *Bacillus thuringiensis* toxin active against coleopteran pests wherein said toxin has a molecular weight of approximately 130 kDa and a predicted amino acid sequence as shown in SEQ ID No. 2.

* * * * *

UNITED STATES PATENT AND TRADEMARK OFFICE
CERTIFICATE OF CORRECTION

PATENT NO. : 5,366,892            Page 1 of 2

DATED : November 22, 1994

INVENTOR(S) : Luis Foncerrada, et al

It is certified that error appears in the above-indentified patent and that said Letters Patent is hereby corrected as shown below:

Column 3, line 34: Delete "government" and insert --governmental--.

Column 4, line 34: Delete "Humanson" and insert --Humason--.

Column 6, line 3: Delete "transcriptional regulator" and insert --transcriptional regulatory--.

Column 6, line 39: Delete "function replication" and insert --functional replication--.

Column 8, line 13: Delete "*Excherichia coli*" and insert --*Escherichia coli*--.

Column 10, line 61 & 62: Delete "*Keptinotarsa decemlineata*" and insert --*Lepinotarsa decemlineata*--.

Column 10, line 63: Delete "*B.t.* gene" and insert --*B.t.* toxin gene--.

UNITED STATES PATENT AND TRADEMARK OFFICE
CERTIFICATE OF CORRECTION

PATENT NO. : 5,366,892

DATED : November 22, 1994

INVENTOR(S) : Luis Foncerrada, et al

It is certified that error appears in the above-indentified patent and that said Letters Patent is hereby corrected as shown below:

Column 10, line 67: Delete "lystae" and insert --lysate--.

Column 11, line 8: Delete "generate" and insert --regenerate--.

Column 21, line 27: Delete "polynucleotide DNA" and insert polynucleotide--.

Signed and Sealed this

Eleventh Day of April, 1995

Attest:

BRUCE LEHMAN

Attesting Officer

Commissioner of Patents and Trademarks